(12) United States Patent
Brewer et al.

(10) Patent No.: US 8,444,627 B2
(45) Date of Patent: May 21, 2013

(54) RESPIRATORY MANIFOLD WITH BRIDGE

(75) Inventors: John Brewer, Marietta, GA (US);
Cassandra E. Morris, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 366 days.

(21) Appl. No.: 12/644,098

(22) Filed: Dec. 22, 2009

(65) Prior Publication Data

US 2010/0163051 A1 Jul. 1, 2010

Related U.S. Application Data

(63) Continuation-in-part of application No. 12/347,422, filed on Dec. 31, 2008.

(51) Int. Cl.
*A61M 39/00* (2006.01)
*A61M 16/00* (2006.01)

(52) U.S. Cl.
USPC .................. 604/533; 604/284; 128/200.24

(58) Field of Classification Search
USPC ..... 604/533–535, 537–539, 284; 128/200.24, 128/201.05
See application file for complete search history.

(56) References Cited

U.S. PATENT DOCUMENTS

| | | | |
|---|---|---|---|
| 1,964,474 A | 6/1934 | Lindquist | |
| 3,978,854 A | 9/1976 | Mills, Jr. | |
| 4,240,417 A | 12/1980 | Holever | |
| 4,351,328 A | 9/1982 | Bodai | |
| 4,569,344 A | 2/1986 | Palmer | |
| 5,220,916 A | 6/1993 | Russo | |
| 5,409,455 A * | 4/1995 | Belden | 604/43 |
| 5,694,922 A | 12/1997 | Palmer | |
| 5,730,123 A | 3/1998 | Lorenzen et al. | |
| 5,735,271 A | 4/1998 | Lorenzen et al. | |
| 6,012,451 A | 1/2000 | Palmer | |
| 6,415,789 B1 | 7/2002 | Freitas et al. | |
| 6,494,203 B1 | 12/2002 | Palmer | |
| 6,612,304 B1 | 9/2003 | Cise et al. | |
| 6,615,835 B1 | 9/2003 | Cise et al. | |
| 6,935,339 B2 | 8/2005 | Mattar Neto et al. | |
| 7,188,623 B2 | 3/2007 | Anderson et al. | |
| 7,191,782 B2 * | 3/2007 | Madsen | 128/207.14 |
| 7,263,997 B2 * | 9/2007 | Madsen et al. | 128/207.14 |
| 7,556,041 B2 | 7/2009 | Madsen | |
| 2002/0078963 A1* | 6/2002 | Rouns et al. | 128/207.16 |
| 2007/0282250 A1* | 12/2007 | Anderson et al. | 604/35 |
| 2008/0210242 A1 | 9/2008 | Burk et al. | |

OTHER PUBLICATIONS (ISO) International Standard 5356, "Anaesthetic and Respiratory Equipment—Conical Connectors. Part 1: Cones and Sockets," Third Edition, 2004, 21 pages.

* cited by examiner

*Primary Examiner* — Quynh-Nhu H Vu
(74) *Attorney, Agent, or Firm* — James B. Robinson

(57) ABSTRACT

A respiratory manifold is provided which has a base port that is coupled to a central body. The central body has at least one laterally-positioned arm having a port. The base port includes a bridge to guide an object moved through one port into the body of the manifold and through the base port to a tracheal tube without folding, twisting, bunching or buckling of any portion of the object within the manifold.

7 Claims, 5 Drawing Sheets

US 8,444,627 B2

RESPIRATORY MANIFOLD WITH BRIDGE

This application is a continuation-in-part and claims the benefit of U.S. application Ser. No. 12/347,422, filed Dec. 31, 2008.

BACKGROUND

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to easily, efficiently, and safely accomplish the multiple therapies in the best interest of the patient has been and continues to be a concern.

When patients receive multiple respiratory therapies or treatments while intubated, problems may occur with the respiratory access manifold, among others. There is a need to provide a common manifold through which all necessary devices are coupled in order to reduce infection. Such a common respiratory access manifold desirably has multiple ports, and a majority of the ports desirably allow some degree of movement to reduce the forces acting on the tracheal tube. Such a manifold desirably permits quick and easy coupling and removal of a variety of devices without compromising the quality of health care provided to the patient. Such a device desirably operates well in a closed circuit ventilating system.

One problem that has been found with multiple device manifolds is that certain devices such as long, thin suction catheters, may become caught on the inner portion of the body of the manifold and/or against the proximal end of a tracheal tube and may bunch up or become stuck. A manifold that avoids the problem of catheter catching and bunching is desirable.

SUMMARY

In response to the difficulties and problems discussed herein, a respiratory manifold is provided. The manifold includes a base port having an inner sleeve that is rotatable relative to the base port, i.e., a swivel. The base port also has a central body with at least one arm, each arm having a lateral port coupled to the central body. Each lateral port has an inner sleeve that is rotatable relative to the lateral port, i.e., a swivel. The manifold also has a proximal port coupled to the central body. The base port, the central body, each arm and its lateral port and the proximal port cooperate to provide a passageway between, for example, a closed suction catheter device and a tracheal tube.

The base port includes a bridge to guide the suction catheter or other tubular object into through the base port to a tracheal tube coupled to the base port without any portion of the tubular object folding, twisting, bunching or buckling within the manifold.

DETAILED DESCRIPTION

Figure 1:
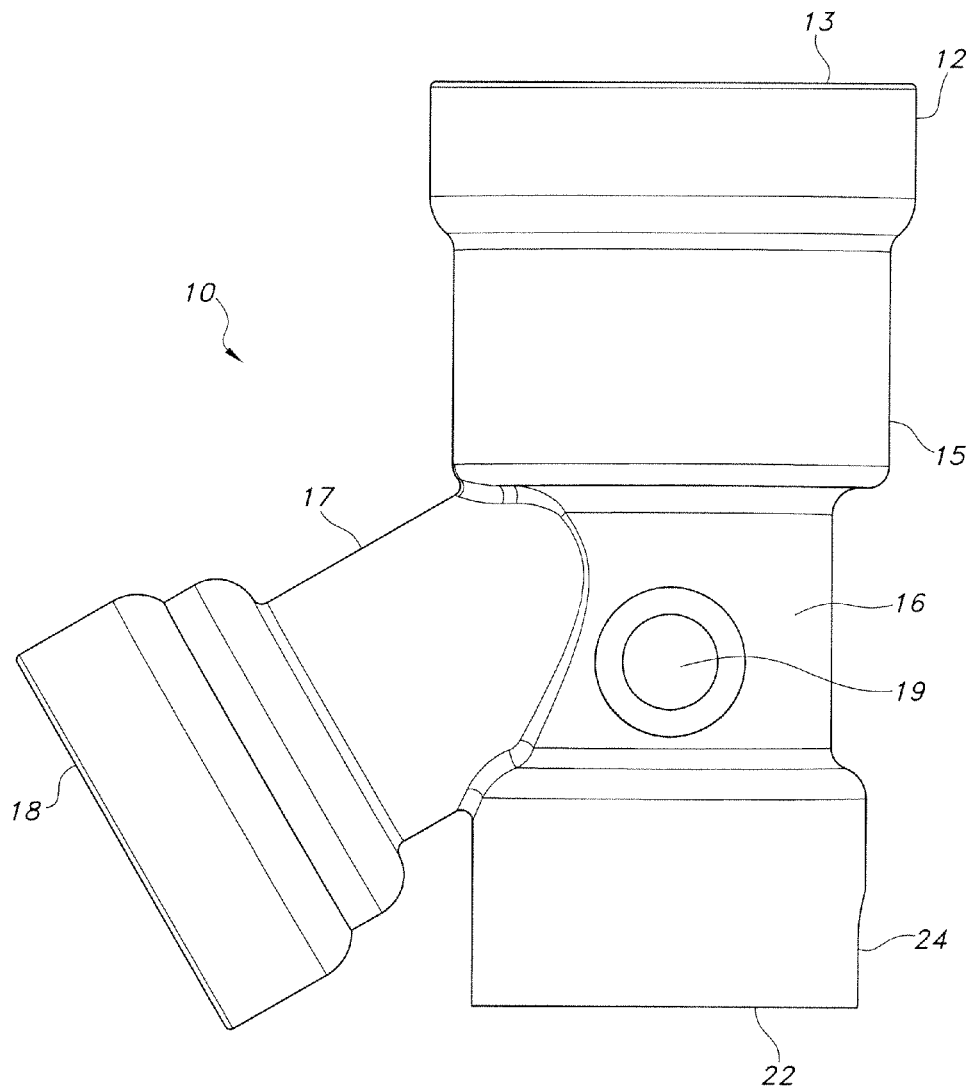
FIG. 1 is a plan view of a respiratory double manifold.

Reference will now be made in detail to one or more embodiments and examples which are illustrated in the drawings. Features illustrated or described as part of one embodiment may be used with another embodiment to yield a still further embodiment.

As used herein the following terms have the specified meanings, unless the context demands a different meaning, or a different meaning is expressed; also, the singular generally includes the plural, and the plural generally includes the singular unless otherwise indicated.

As used herein, the term "port" means a structure providing an opening into or through a component for the passage of an object and/or a liquid and/or a gas.

As used herein the term "suction catheter" means long, flexible tubes used to remove secretions from the airway and are available in many sizes, typically from 10 to 25 inches (25 to 64 cm) in length. Suction catheters are flexible and may be made from latex and other soft polymers. The inner and outer diameters will vary according to the catheter size chosen by a user as appropriate for his particular application, e.g. pediatric or adult. Catheter sizes are usually expressed as "French" and common catheter sizes range from a 5 French to an 18 French. (Note, French is a measure of circumference based on the theory that non-round tubes of the same circumference will fit into the same incision. One French is approximately 0.33 mm or 0.013 inch). The catheter may generally have an outer diameter of about 0.165 to about 0.205 inch (4.19 to about 5.21 mm).

Suction catheters are well known and widely commercially available for many medical uses. Suctioning may be performed using an "open" or "closed" system. In the open system, the suction catheter is merely a flexible plastic tube that is inserted into a tracheal tube like an endotracheal tube or tracheostomy tube, with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" device and is available under the tradename TRACH CARE® from BALLARD® Medical Products (Kimberly-Clark Corporation) or KIMVENT®. As the patient requires artificial removal of secretions, the suction catheter may be advanced through one end of the plastic bag, through a connecting fitting or manifold and into the tracheal tube. The other, proximal end of the suction catheter is attached to a source of suction. Suction may be applied using, for example, a finger controlled valve on the proximal end of the suction catheter, and the secretions removed. Secretions are thus drawn into the lumen of the suction catheter tube and removed and the system remains closed. The suction catheter is subsequently withdrawn from the flexile lumen and back into the plastic bag to keep the circuit closed. Closed suction systems are generally preferred by healthcare providers since the provider is better protected from the patient's secretions.

Closed suction systems are also easier and quicker to use since a sterile field need not be created each time the patient must be suctioned, as is required in open suction systems. The closed suction catheter may be permanently attached to the proximal end of the tracheal tube or may be detachably connected so that it may be replaced periodically.

Examples of other types of generally tubular objects that may be inserted into the tracheal tube and thence into the lungs include bronchoscopes and bronchoalveolar lavage (BAL) catheters. One type of bronchoalveolar lavage catheter is commercially available under the trade name BAL CATH® from Ballard Medical Products Inc., a division of Kimberly-Clark Corporation and may be used for lavage and sampling of the lungs to assist in the diagnosis of ventilator acquired pneumonia.

Manifolds that couple to a tracheal tube, a ventilator, and a suction catheter assembly provide a plurality of openings or ports. U.S. patent application Ser. No. 12/347,422, for example, provides a swivel manifold that permits multiple access for additional objects, devices or instruments, and reduces or removes the need to open a closed ventilating system. A double swivel manifold, as illustrated in the Figures, provides access for an object in addition to the tracheal tube. Either type may incorporate the disclosed improvement. The double swivel is shown for ease of illustration.

Figure 2:
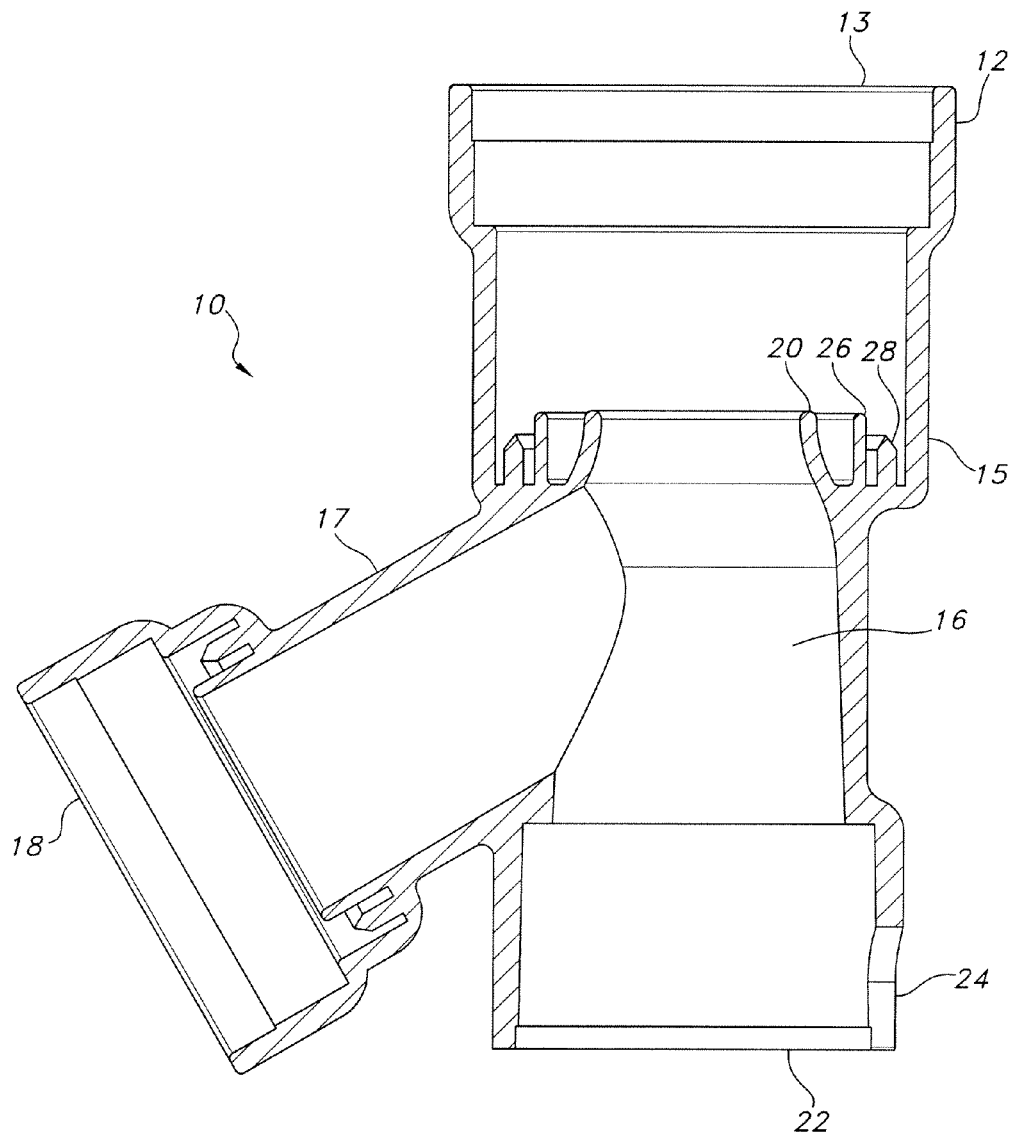
FIG. 2 is a cross-sectional view of FIG. 1.
Figure 3:
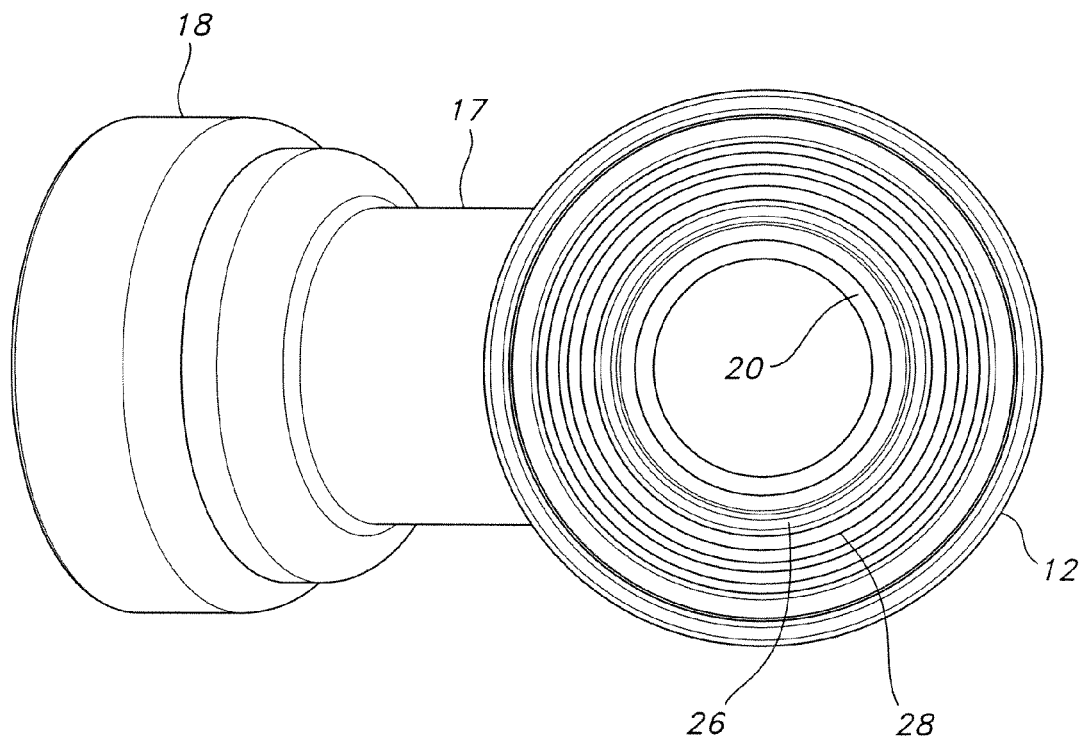
FIG. 3 is an end view of the embodiment of FIG. 1.

Turning now to the drawings, as illustrated in FIGS. 1-3, a respiratory swivel manifold 10 is provided. The manifold 10, as shown in FIGS. 1 and 2, includes a hollow, cylindrically-shaped distal base port 12 which desirably, couples at its distal end 13 to a proximal end of a tracheal tube 14 (not shown). The base port 12 includes a generally hollow cylindrically-shaped central body 16 that is desirably axially aligned with the base port 12 and that is provided on a distal end 15 of the base port 12. The central body 16 is formed to include at least one generally cylindrically-shaped arm 17, having a lateral port 18 provided thereon. A hollow, generally cylindrically-shaped proximal port 22 is formed on a proximal end 24 of the central body 16. A "bridge" 20 is included on the distal end of the central body 16. The bridge 20 serves to align the suction catheter as it is passed into the manifold. The bridge 20 desirably has a smooth transition from the body 16 in order to avoid a sharp edge or protruding ledge with which an object could catch and be impeded.

Moving concentrically outward from the bridge 20 are two annular slots 26, 28 for the anchoring of a swivel (not shown). The swivel has sealing ribs or prongs that seat within the two annular slots 26, 28. The annular slots 26, 28 do not affect the movement of a catheter 30. More information on the annular slots and cooperating sealing ribs may be found in U.S. Pat. No. 5,694,922, particularly FIGS. 5 and 6.

It can be seen that the ports 12, 18 and 22 and central body 16 cooperate to provide an opening or passageway therethrough. While the ports 12, 18 and 22 and body 16 are generally provided on the same plane, it will be appreciated that this is not intended as a limitation, and the ports 12, 18 and 22 and/or body 16 may each, or in combination, be formed on separate planes and/or axes. Further, while the configuration(s) herein will often be described as "generally cylindrical", it will be understood that this description is not intended as a limitation, and that any configuration or combination of configurations which operate as shown and/or described herein may be utilized.

Turning to FIG. 3 that is a view looking into the manifold 10 on the distal base port 12 end, the bridge 20 can be seen clearly.

The base port 12 and the lateral port 18 each permit a device coupled thereto to rotate freely. This rotation greatly reduces the pressure and/or torque produced by devices coupled to these ports (not shown). Moreover, such devices are not likely to become or remain twisted, due to the rotation allowed by the swivels in the ports. This reduction in pressure and/or torque results in reduced pressure and/or torque exerted on the tracheal tube which results in less pressure and/or torque exerted in the patient's throat. In addition, it permits a health care provider more freedom to maneuver various devices, since such devices will not likely become, or remain, twisted when coupled to the ports 12, 18 of the manifold 10.

The manifold 10 desirably positions the lateral port 18 away from the base port 12, and the lateral port 18 is desirably provided at an angle of less than about 90 degrees from the axis of the base port 12 and the proximal port 22. It will be understood that one or more ports may be positioned in another plane or axis. The lateral port 18 is desirably at an angle of about 60 degrees from the axis of the base and proximal ports.

The manifold 10 is desirably formed from a hard plastic polymer. Suitable polymers include polycarbonate, an acrylic, nylon, polyolefins and the like and combinations thereof. The manifold 10 is desirably transparent though this is not required. The manifold may be opaque or translucent. It the manifold is opaque a transparent area or viewing port 19 may be provided through which the interior may be viewed. This is helpful in watching the advancement of a catheter 30 into the tracheal tube 14.

Figure 4:
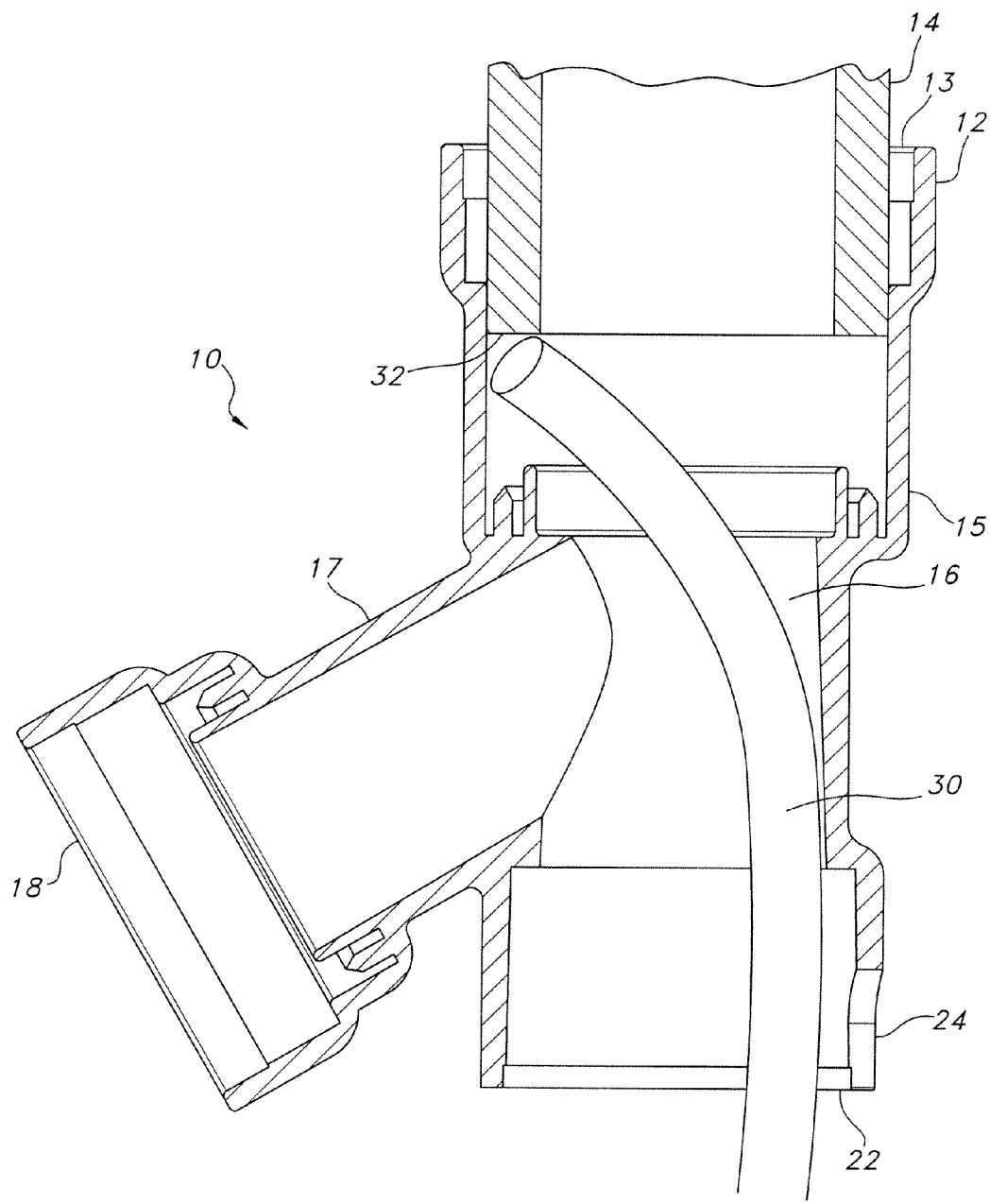
FIG. 4 is a cross-sectional view of a manifold without a bridge.
Figure 5:
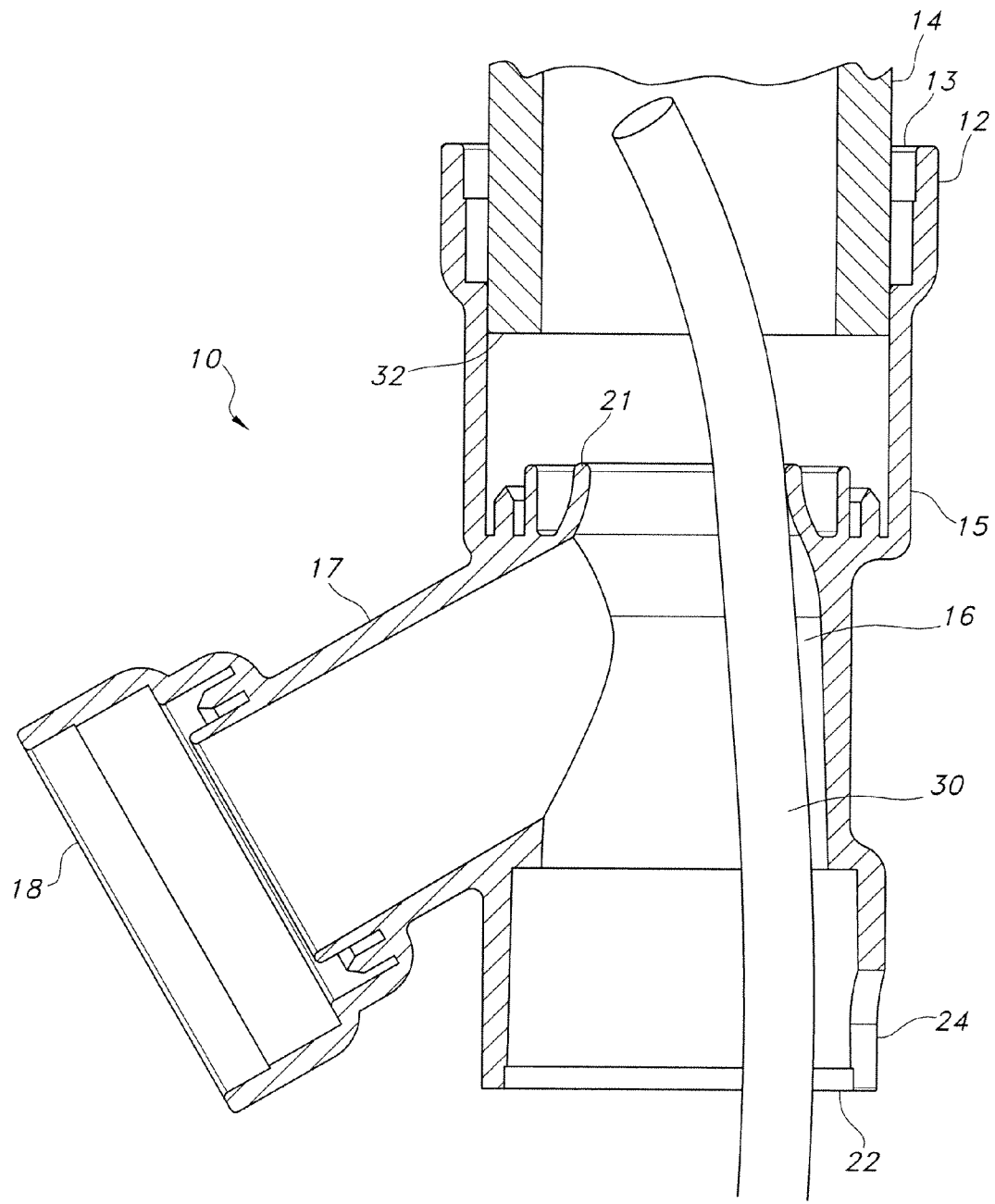
FIG. 5 is a cross-sectional view of a manifold with a bridge.

Respiratory accessory devices are frequently formed from very soft materials, and easily buckle, fold, and bunch if they encounter any irregularity, protuberance, protrusion, or obstruction within the inner surface of the manifold. It has been found that on manifolds without the bridge, the distance from the proximal end port 22 to the point where the bridge 20 is provided herein allows a suction catheter 30 to bend. Without a bridge, that bending may result in the catheter 30 becoming stuck in the opening between the body 16 and the port 12. The bridge 20 acts as a ramp or guide that assists in directing the catheter to help prevent bending and, in the worst case, buckling, of the catheter. FIGS. 4 and 5 illustrate the effect of the bridge. In FIG. 4 a manifold 10 without a bridge 20 is shown with a catheter 30 inserted and in FIG. 5 a manifold 10 with a bridge is shown with a catheter 30 inserted. The proximal end 32 of a tracheal tube 14 is connected to the manifold's (distal) base port 12 and part of the tube 14 is shown as well. As the catheter 30 is advanced into the manifold without the bridge, the catheter 30 may contact the most proximal end 32 of the tracheal tube 14. This may cause the catheter 30 to get stuck or jammed against the tube end 32 and bend or curl. FIG. 5, in contrast, shows that the catheter 30 is successfully passed into tracheal tube 14 because the bridge 20 acts to center or guide the catheter 30 and so avoid the proximal end 32 of the tube 14.

Suction catheters 30 may generally have an outer diameter of about 0.165 to about 0.205 inch (4.19 to about 5.21 mm). The inner diameter of the bridge 20 is, of course, somewhat larger than the catheter 30; in the range of about 6 to 10 mm, more particularly about 9 mm at its narrowest point, which is generally the tip 21. The wall of the bridge 20 may have a thickness of from about 0.5 mm to 3 mm, more particularly from 1 to 2 mm and still more particularly about 1.5 mm. The height of the bridge 20 may be between 2 and 6 mm, more particularly between 2.5 and 5 mm and still more particularly about 3.5 mm. The height of the bridge 20 is subject to limitation by the International Standard ISO 5356-1:2004 (E), which specifies the clearance distance required from the distal tip 21 of the bridge 20 to the distal end 13 of the base 12 in order to allow space for the insertion of the tracheal tube.

The base port 12 is sized to connect to a tracheal tube and so has a diameter of about 15 mm (with the swivel in place). The lateral port 18 is the same size as a tracheal tube since it is designed for connection to a ventilator.

As will be appreciated by those skilled in the art, changes and variations to the invention are considered to be within the ability of those skilled in the art. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A respiratory manifold, comprising:
   a base port, wherein the base port includes an inner sleeve that is rotatable relative to the base port;
   a central body coupled to the base port having at least one arm, each arm having a lateral port, and each of said lateral ports having an inner sleeve that is rotatable relative to the lateral port; and
   a proximal port coupled to the central body,
   wherein the base port, the central body, each of said lateral ports and the proximal port cooperate to provide a passageway, wherein said at least one arm and its lateral port is positioned at an angle in a range of less than 90 degrees relative to the central body, and;
   wherein the base port includes a bridge between said lateral port and said base port, the bridge having a smooth transition from the body to direct an object moved through at least one port into the passageway and through the base port to a tracheal tube coupled thereto, without folding, twisting or bunching of any portion of the object within the manifold.

2. The respiratory manifold of claim 1, further comprising a second arm positioned at an angle of about 60 degrees relative to the central body.

3. The respiratory manifold of claim 1, wherein said bridge has a diameter of from 6 to 10 mm.

4. The respiratory manifold of claim 1, wherein said object is a suction catheter, bronchoscope or bronchoalveolar lavage catheter.

5. The respiratory manifold of claim 4 wherein said tracheal tube is an endotracheal tube.

6. The respiratory manifold of claim 4, wherein said bridge has a diameter of from 6 to 10 mm.

7. A respiratory manifold, comprising:
   a base port, wherein the base port includes an inner sleeve that is moveable relative to the base port;
   a central body coupled to the base port;
   a proximal port coupled to the central body,
   at least one arm at an angle of about 60 degrees relative to an axis between the base and proximal ports, each of said arms having a lateral port, each of said lateral ports having an inner sleeve that is moveable relative to its lateral port, and;
   wherein the base port, the central body, each of said lateral ports and the proximal port cooperate to provide a passageway, and;
   wherein the base port includes a bridge between said lateral port and said base port, the bridge having a smooth transition from the body to direct a suction catheter moved through the proximal port into the passageway and through the base port to a tracheal tube coupled thereto without folding, twisting or bunching of any portion of the catheter within the manifold.

* * * * *